(12) United States Patent
Basiony

(10) Patent No.: US 11,547,475 B2
(45) Date of Patent: Jan. 10, 2023

(54) SYSTEM FOR ITS USE IN THE TREATMENT OF VASCULAR STENOSIS AND OCCLUSIONS

(71) Applicant: Mohamed A Basiony, Kenmore, WA (US)

(72) Inventor: Mohamed A Basiony, Kenmore, WA (US)

( * ) Notice: Subject to any disclaimer, the term of this patent is extended or adjusted under 35 U.S.C. 154(b) by 808 days.

(21) Appl. No.: 16/550,243

(22) Filed: Aug. 25, 2019

(65) Prior Publication Data

US 2020/0061349 A1     Feb. 27, 2020

Related U.S. Application Data

(60) Provisional application No. 62/723,149, filed on Aug. 27, 2018.

(51) Int. Cl.
*A61B 18/14* (2006.01)
*A61M 25/10* (2013.01)
*A61B 18/08* (2006.01)
*A61M 1/36* (2006.01)
*A61B 18/00* (2006.01)

(52) U.S. Cl.
CPC ........ *A61B 18/1492* (2013.01); *A61B 18/082* (2013.01); *A61M 25/10186* (2013.11); *A61M 25/10188* (2013.11); *A61B 2018/0041* (2013.01); *A61B 2018/00041* (2013.01); *A61B 2018/00404* (2013.01); *A61B 2018/00422* (2013.01); *A61B 2018/00791* (2013.01); *A61M 1/3661* (2014.02); *A61M 25/104* (2013.01); *A61M 2025/1079* (2013.01); *A61M 2205/0211* (2013.01); *A61M 2205/18* (2013.01); *A61M 2205/3653* (2013.01)

(58) Field of Classification Search
CPC .......... A61B 18/082; A61B 2018/0041; A61B 2018/00422; A61B 2018/00404
See application file for complete search history.

(56) References Cited

U.S. PATENT DOCUMENTS

| | | | | |
|---|---|---|---|---|
| 4,654,024 A | * | 3/1987 | Crittenden | A61B 18/28 219/121.76 |
| 4,832,048 A | * | 5/1989 | Cohen | A61B 18/1492 606/41 |
| 5,318,525 A | * | 6/1994 | West | A61B 18/1492 604/95.04 |
| 6,210,408 B1 | * | 4/2001 | Chandrasekaran | A61M 25/10 606/41 |
| 2011/0118735 A1 | * | 5/2011 | Abou-Marie | A61B 18/1492 606/45 |

* cited by examiner

*Primary Examiner* — Jaymi E Della

(57) ABSTRACT

A system to be used inside a dialysis unit for dilating obstructed blood vessel, comprises a catheter, a device, a remote-control box, supportive components and connection cables. A catheter comprises an elongated portion, a proximal end and a distal end, extended longitudinally. A distal end of a catheter has a convectively heating tip with a heat generating element and an inflatable balloon. A device has a radiofrequency current generator to supply and control a heating process of a heat generating element of a catheter tip. A remote-control box comprises a valve assembly, a heat activation switch and a balloon inflation switch to facilitate a treatment process.

13 Claims, 6 Drawing Sheets

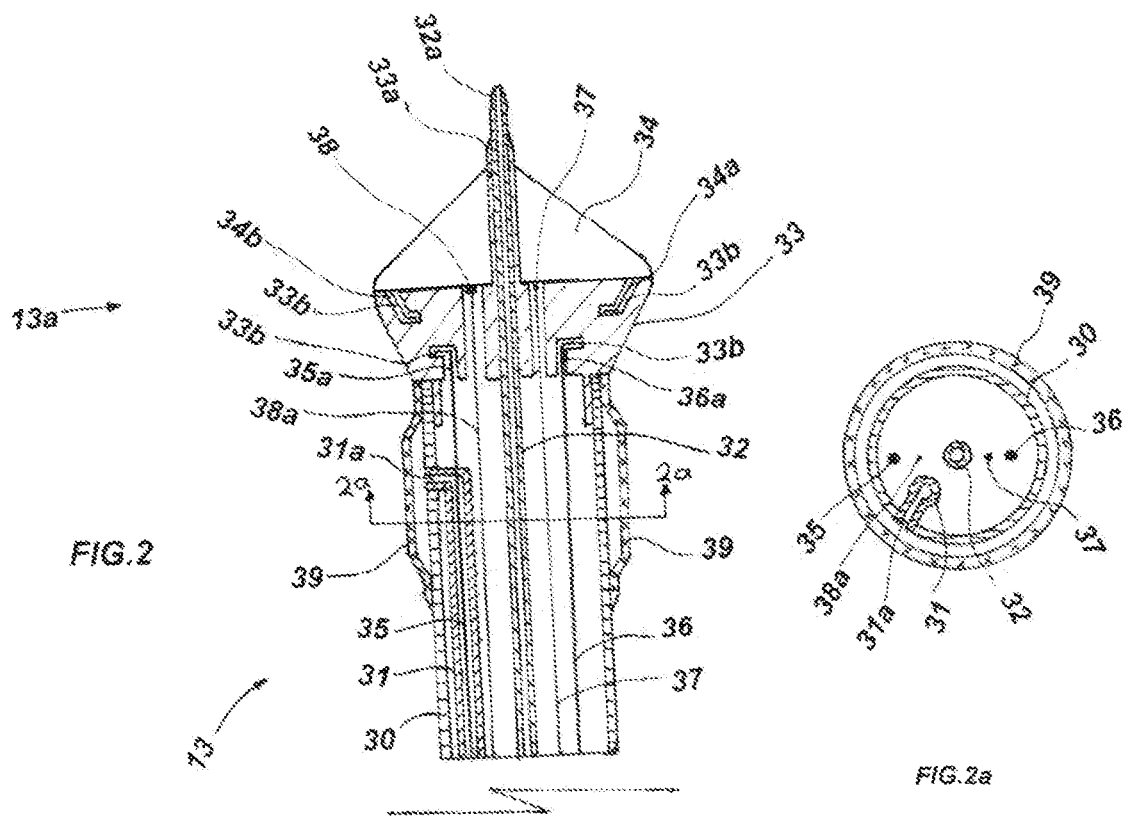
FIG.2
FIG.2a
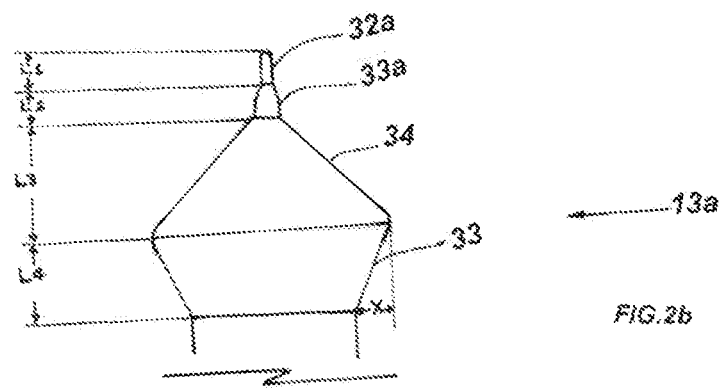
FIG.2b

SYSTEM FOR ITS USE IN THE TREATMENT OF VASCULAR STENOSIS AND OCCLUSIONS

BACKGROUND

Vascular stenosis is defined as a narrowing or constriction to the body or opening of a vessel conduit. Such narrowing may range from a minimal to occlusion of an entire vessel lumen. Central venous stenosis (CVS) is commonly seen in patients receiving hemodialysis through central venous catheters (CVC).

The precise mechanism of central venous catheters (CVC)-associated central venous stenosis (CVS) remains largely undefined. It is thought that number of factors associated with the catheters themselves, the position of the foreign body against the vessel walls, as well as the uremic milieu and consequent inflammational interact to produce central venous stenosis (CVS).

Furthermore, direct physical damage from the movement of the catheter tip or body against a vessel wall can potentially result in thrombin generation, platelet activation, expression of P-selectin and an inflammatory response.

The development of central venous stenosis (CVS) in the dialysis patient is a serious issue, and it has a greater impact compared with stenosis of a peripheral vein because the central veins represent the final common pathway for blood flow from the periphery to the heart. If central stenosis is allowed to progress, the hemodialysis vascular access may eventually be lost. In addition, the development of central vein obstruction obviates the possibility of creating a new vascular access on the affected side. An unfortunate consequence of the loss of central vein patency for the patient is diminished life expectancy.

The early 1990s witnessed a move away from the subclavian vessels toward the jugular veins due to the association between subclavian vein cannulation for hemodialysis access and subsequent central venous stenosis (CVS) that was identified in the 1980s, when the subclavian approach was widely regarded as the safest and easiest method. However, the internal jugular route has not fulfilled its early promise of minimal central venous stenotic complications.

The treatment of central venous stenosis (CVS) can be divided into three clinical choices, angioplasty (PTA), angioplasty with stent placement (PTS) and surgery. It is handled by either interventional nephrologists or vascular surgeons.

So, there is a need to develop a safe, easy and efficient system to help the nephrologists to deal with central venous stenosis (CVS) within a dialysis department as a routine catheters maintenance to quickly deal with rapid stenosis progression and to early treat every significant access stenosis and occlusion. Plus, also with a relatively less cost treatment without patient's exposure to anesthesia, radiation and contrast agents.

SUMMARY

Accordingly, a system comprises a catheter, a device, a remote-control box, supportive components and connection cables is described to may address the above issues.

A catheter with convectively heating tip along with an inflatable balloon may be used for dilating obstructed blood vessel, specially that is related to hemodialysis catheters that are used for hemodialysis treatments. A resulting convective heat transfer to an interior blood vessel wall may seal the plaque and endothelium to the intima of a blood vessel without the tissue denaturation and to may promote restoration and healing of a treated region of a blood vessel.

A catheter comprises an elongated portion, a proximal end and a distal end, extended longitudinally. Elongated portion has an outer tube, an inner tube, a side tube, two stylets on each side of an elongated portion, a single radiofrequency lead and temperature sensor leads. These are extended between a distal end and a proximal end.

A distal end of a catheter has a soft distal tip of an inner tube, a distal end of an outer tube, a distal end of a side tube with its lateral passage to inflate an inflatable balloon, an inflatable balloon, a ceramic portion, a distal tip of a ceramic portion, a heat generating element that is axially aligned with a ceramic portion, a temperature sensor with its distal leads, a distal end of a single radiofrequency lead and distal ends of two stylets.

A proximal end of a catheter has a proximal end of an inner tube, a proximal end of an outer tube, a proximal end of a side tube with its proximal extension, a proximal end of two stylets, a proximal end of a single radiofrequency lead, a proximal end of a temperature sensor leads, a coupling assembly and a syringe attached to a coupling assembly with its tip and plunger.

A device provides a heat generating element of a catheter distal tip with a necessary energy. A device has a radiofrequency current generator to supply and control the energy supplied to a heat generating element. Also, a device has an OFF/ON switch, an alarm LED, a radiofrequency energy control, a display, a time set/monitor for a heating period of a heat generating element, a time set/monitor for an inflation period of an inflatable balloon, a temperature set knob, a screen to monitor a setting temperature and an actual temperature that is measured by a temperature sensor and a patient ground plate.

A system also, includes a remote-control box which comprises a valve assembly, a proximal extension of a side tube, a fixation portion of a proximal extension of a side tube, a heat activation switch with its cover and magnets, and a valve control switch with its cover and magnets.

BRIEF DESCRIPTION OF THE DRAWINGS

The accompanying drawings, which are incorporated in, and constitute a part of the specification, illustrate or exemplify embodiment of the present implementation and, together with the description, generally explain the principles and features of the present implementation. The drawings are briefly described as follows:

FIG. 2 is an enlarged perspective view of the distal end of the catheter of the system of FIG. 1 according to the present disclosure.

FIG. 2a is a cross sectional view of the distal end taken along the line 2a-2a of the catheter of the system of FIG. 1 according to the present disclosure.

FIG. 2b is an enlarged perspective view of the tip of the catheter of the system of FIG. 1 according to the present disclosure.

DETAILED DESCRIPTION

Figure 1:
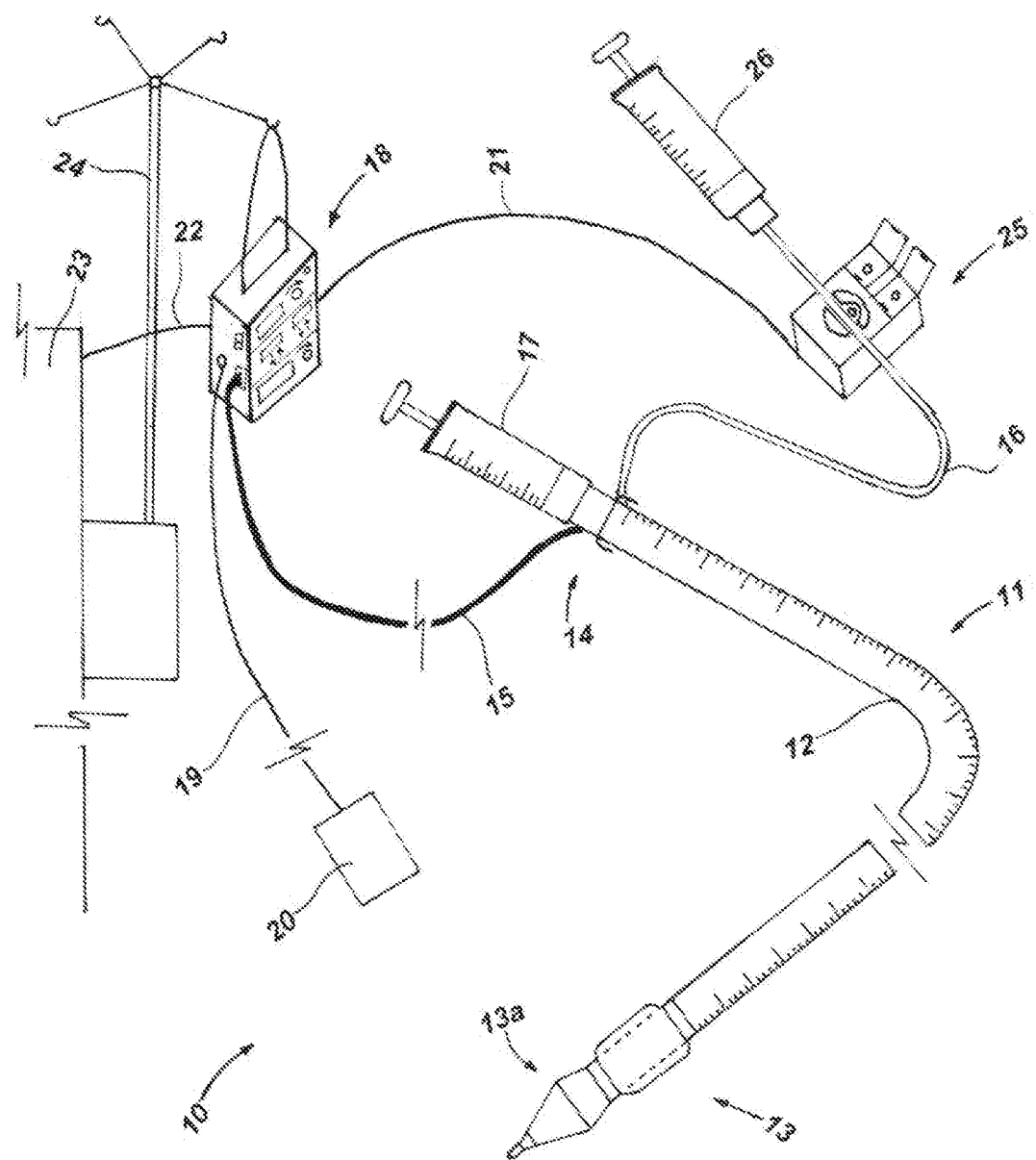
FIG. 1 illustrates a perspective view of the system with its components according to the present disclosure.

The following detailed description illustrates the principal of the disclosure by way of example not by way of limitation. While a reference use of the present disclosure describes a system to be used for the treatment of vascular stenosis and occlusions, in particularly that are related to hemodialysis catheters, additional non-limiting usage would also include dilating the stenosis within arteries and veins, as those of ordinary skill in the art will readily understand. Also, it will be understood that the system may also be used for other types of treatments with or without the inflatable balloon, consequently, the scope of the implementation is not to be limited by the field to which the implementation is applied.

A system of present disclosure comprises a catheter, a device, a remote-control box, supportive components and connection cables.

A catheter of a system has a convectively heating tip along with an inflatable balloon to may be used for dilating obstructed blood vessel, specially that is related to hemodialysis catheters. The resulting convective heat transfer to an interior blood vessel wall may seal a plaque and endothelium to the intima of a blood vessel without a tissue denaturation and to may promote restoration and healing of treated region of a blood vessel.

Using convectively heating tip and an inflatable balloon may have an advantage compare to using only a conventional inflatable balloon without heating, as using a conventional inflatable balloon without heating may compress a plaque outwardly into a vessel wall and such outward compression may result in stress on a vessel wall, and may causing cracking, tearing and stretching of the wall. In some cases, after a conventional inflatable balloon catheter (that is used without heating) is removed, torn plaque and tissue become dislodged from a blood vessel wall resulting in abrupt reclosure of a vessel.

A device of a system provides a heat generating element of a catheter tip with a necessary energy to dilate obstructed blood vessel. A device has a radiofrequency current generator to supply and control the radiofrequency energy supplied to a heat generating element of a catheter tip. Using a radiofrequency current has been widely used as the rationale for using radio frequency current is that the frequency is above that which would cause neuromuscular stimulation and permit enough energy dissipation to produce a rapid rise in temperature. Thus, electrical shock does not occur and healing of treated region of a blood vessel is accomplished.

To achieve a healing of a blood vessel without producing excessive heat penetration, is heating a stenosis site at a high temperature for an extremely short period. A nephrologist is going to preset a time on a device and a device will control the energy supplied to a heat generating element.

Thus, a heat generating element must be rapidly heated and rapidly cooled within a specified period controlled by a device to adequately dilating a blood vessel without causing tissue damaged. So, a time from the moment at which a heating process begins until a completion of a heating process is presetting and automatically controlled by a device. This is plus, the heat is only applied to a tip of a catheter and a low thermal conductivity ceramic portion that is axially aligned with a heat generating element may act as an effective means to prevent damage of surrounding tissues, so a generated heat is then transferred primarily to a lumen obstruction of a blood vessel.

No referring to FIG. 1, it illustrates a system 10 comprises a catheter 11, a device 18, a remote-control box 25 and other supportive components and cables, as follows;

A catheter 11 of a system 10 comprises an elongated portion 12, a proximal end 14 and a distal end 13, extended longitudinally. A catheter may have different sizes between 6 to 16 French circumferences, or any other suitable sizes. A length of a catheter may be between 10 cm to 55 cm or any other suitable length.

An elongated portion 12 of a catheter 11 may have an exterior with generally round, oval or any other shapes in cross section and may have an internal longitudinally extending lumen of circular shape, or any other shapes.

A proximal end 14 of a catheter 11 has a cable 15 that represents an extension of a single radiofrequency lead and temperature sensor leads that are connected to a device 18 for control and monitor. Also, a proximal end 14 has a proximal extension 16 of a side tube 31 FIG. 2 that is fixed on a surface of a remote-control box 25 and connected to a syringe 26. Also, a proximal end 14 of a catheter 11 is connected to a syringe 17.

A distal end 13 of a catheter 11 has a distal tip 13a.

A device 18 of a system 10 is connected to a remote-control box 25 via a cable 21. A device 18 is preferably hanging on IV Pole 24 of a dialysis machine 23 and receives its power from an auxiliary power socket (not shown for simplicity) of a dialysis machine 23. In another implementation a device 18 receives its power from a wall source and hanging on a standalone IV pole. A device 18 also is connected to a patient ground plate 20 via a cable 19 and connected to a catheter 11 via a cable 15.

FIG. 2 illustrates an enlarged perspective view of a distal end 13 of a catheter 11, wherein an outer tube 30 and a side tube 31 which is used to inflate the inflatable balloon 39 via a lateral passage 31a using a syringe 26 that is connected to a proximal extension 16 of a side tube 31. Also, in FIG. 2, an inner tube 32 which has a soft tip 32a to prevent damage to a blood vessel during insertion of a catheter 11 and to facilitate advancement through a blood vessel. A soft tip 32a may be coated by a radiopaque material for a fluoroscopic observation.

An outer tube 30, a side tube 31 and inner tube 32 may be made by a biocompatible material like; polyethene, polycarbonate, silicon or any other suitable material. In another implementation, an outer tube 30, a side tube 31 and an inner tube 32 may be made by different materials.

An inflatable balloon 39 may have a conventional construction with a length in a range from about 2 to 5 cm or any suitable length, and a diameter when fully inflated in the range from about 4 mm to 30 mm or any other suitable diameter. An inflatable balloon 39 may be constructed of a same material of the catheter 11 such as polyethene, polycarbonate, silicon or any other suitable material and it may be coated by a radiopaque material for a fluoroscopic observation.

Still referring to FIG. 2, a ceramic portion 33 that may have a low thermal conductivity such as zirconia ceramics and may act as an effective means to prevent surrounding tissues of stenosis area from burning and damage. A ceramic portion 33 has a distal tip 33a with a tapered distal end for easy insertion of a catheter 11. Also, a ceramic portion 33 has four cavities 33b, two of said cavities are used to fix hooks 34a and 34b of a heat generating element 34 and other two of said cavities are used to fix hooks 35a of a first stylet 35 and 36a of a second stylet 36.

A ceramic portion 33 has a smooth surface that is ground like a mirror surface with roughness of 1 Ra or better. A distal tip 33a of a ceramic portion 33 may be coated by a radiopaque material for a fluoroscopic observation as a soft distal tip 32a of an inner tube 32.

A first stylet 35 and a second stylet 36 are located on each side of a catheter 11 and may be acting as reinforced members to facilitate a catheter 11 insertion and advancement through a blood vessel. Stylets 35 and 36 may preferably made of super elastic material or stainless steel and may have a diameter of 0.08 inch to 0.038 inch or any other suitable diameter.

Also, in FIG. 2, a heat generating element 34 has a conical shape or any other suitable shapes. It also has two hooks 34a and 34b that are used to be fixed inside cavities 33b of a ceramic portion 33, to fix a heat generating element 34 to a ceramic portion 33. Also, a proximal straight end of a heat generating element 34 contacts with a temperature sensor 38 to measure an actual temperature of a heat generating element 34 which is also a temperature of stenosed area that is surrounding a heat generating element 34 and contacts with a single radiofrequency lead 37 to provide a heating energy from a device 18 to a heat generating element 34. A temperature sensor 38 has leads 38a to be connected to a device 18 for an actual temperature reading, display and control.

A heat generating element 34 may be made of a metal such as surgical stainless steel or any other suitable materials. Also, a heat generating element 34 may have a unit heat capacity of about less than one joule/degree C. An exterior surface of a heat generating element 34 may be coated with a non-stick surface to do not stick to a blood vessel tissue. Also, a heat generating element 34 my have a sufficient mass to avoid burn-through during use and to provide a sufficient heat for treatment.

Hooks 34a, 34b, 35a and 36a that are fixed inside cavities 33b. A heat generating element 34, a ceramic portion 33 and an outer tube 30 are retained on a distal end 13 of a catheter 11 by appropriate means such as adhesive, an appropriate locking means, or any suitable mean.

FIG. 2a illustrates a cross sectional view of a distal end 13 taken along line 2a-2a, wherein an outer tube 30, an inner tube 32, a side tube 31 with its lateral passage 31a, a first stylet 35, a second stylet 36, a single radiofrequency lead 37 and temperature sensor leads 38a.

FIG. 2b illustrates a catheter tip 13a, wherein a soft distal tip 32a of an inner tube 32, a ceramic distal tip 33a of a ceramic portion 33 and a heat generating element 34. "L1" represents a longitudinal length of a soft distal tip 32a, it may be about 1 mm to about 3 mm or any suitable length. "L2" represents a longitudinal length of a ceramic distal tip 33a, it may be about 1 mm to about 2 mm or any suitable length. "L3" represents a longitudinal length of a heat generating element 34, it may be about 4 mm to about 15 mm or any suitable length. "L4" represents a longitudinal length of a ceramic portion 33, it may be about 3 mm to about 10 mm or any suitable length. "x" represents a distance between an extension of a distal end of a ceramic portion 34 and its proximal end, it may be about 0.3 to about 1.5 French or any other suitable French.

Figure 3:
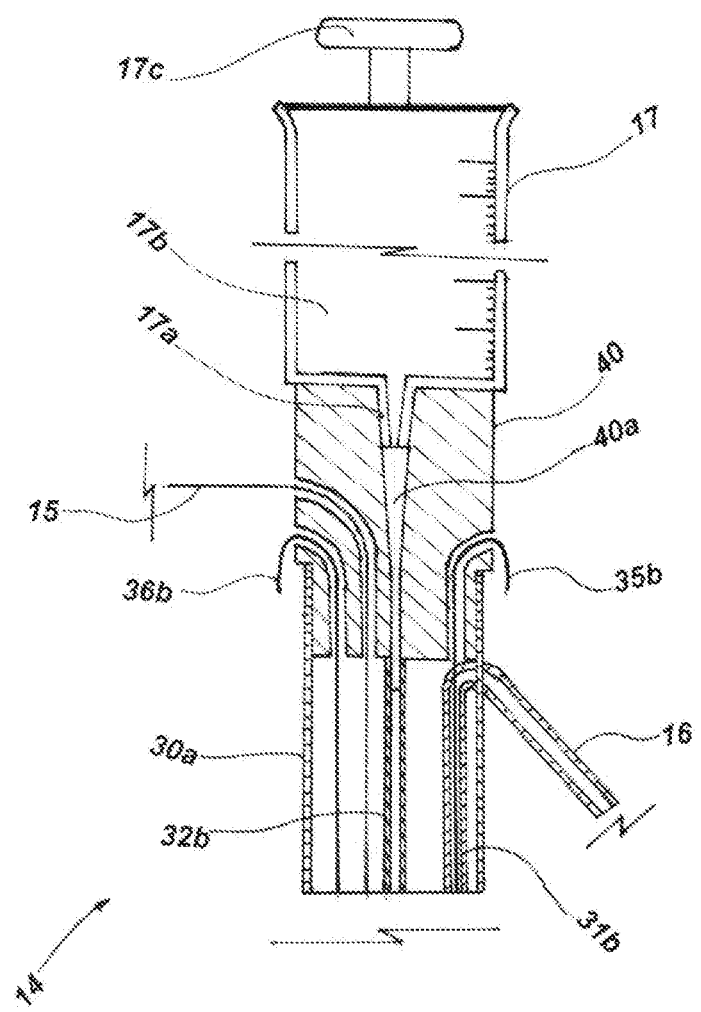
FIG. 3 is an enlarged perspective view of the proximal end of the catheter of the system of FIG. 1 according to the present disclosure.

Now referring to FIG. 3, it illustrates an enlarged perspective view of a proximal end 14 of a catheter 11 of a system 10 wherein, a proximal end of a side tube 31b and its proximal extension 16, a proximal end of an outer tube 30a, a proximal end of an inner tube 32b, a proximal end of a first stylet 35b, a proximal end of a second stylet 36b, a proximal end of a cable 15. A proximal end of a cable 15 represents a proximal end of a single radiofrequency lead 37 and a proximal end of temperature sensor leads 38a.

Also, FIG. 3 illustrates a coupling assembly 40 for sealingly coupled a syringe 17 to a proximal end 14 of a catheter 11. A syringe 17 has a tip 17a that is fluidly connected a syringe lumen 17b to a proximal end 32b of an inner tube 32 via an inner channel 40a of a coupling assembly 40. A syringe 17 is used to push a physiological tolerable flushing liquid (using its plunger 17c) such as a saline solution, a dextrose solution or an oxygen bearing solution to provide an oxygen to tissue downstream of a catheter tip 13a during the operation. Also, a syringe 17 may be used to provide evacuation (suction) of the emulsified thrombus deposits during the operation.

Figure 4:
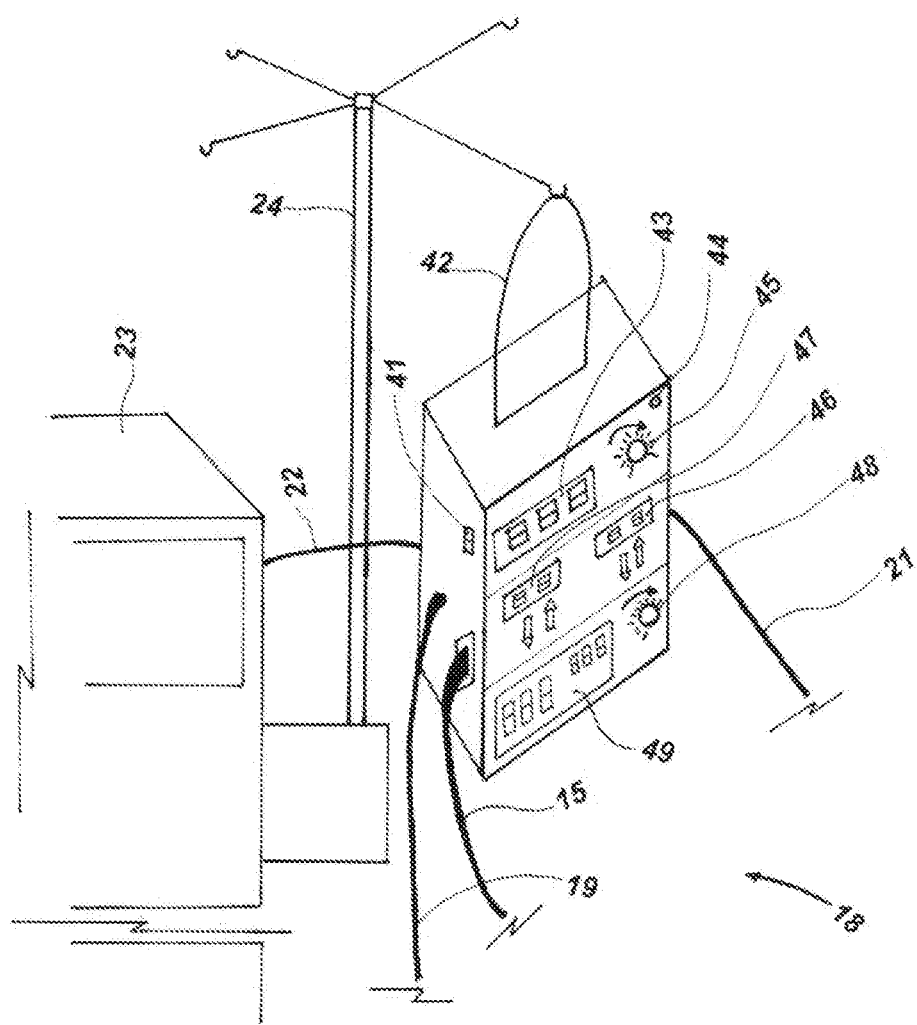
FIG. 4 is an enlarged perspective view of the device of the system of FIG. 1 according to the present disclosure

FIG. 4 illustrates an enlarged perspective view of a device 18 of a system 10 which is used to supply and control an energy supplied to a heat generating element 34 of a distal tip 13a of a catheter 11. A device 18 has a radiofrequency current generator to supply a heating generating element 34 with a necessary radiofrequency energy.

Radiofrequency energy may be safer compare to a direct current or a low frequency power sources as the risk of a physiological response or electrocution response may be reduced at a radiofrequency above 100 Khz. The dissipated electrical energy is converted into heat to produce an adequate heating of stenosis area at a high temperature for an extremely short period of time without processing excessive heat penetration to a blood vessel wall.

A device 18 has an OFF/ON switch 41 to supply power to a device 18, an alarm LED 44 to give audible and visual alarm in case of any mal function and in case any of the essential parameters such as temperature are outside certain pre-setting levels, radiofrequency energy control knob 45 to be set a desired radiofrequency energy, a display unit 43 to display a set radiofrequency energy and alarms, a time set/monitor 46 for a heating period of a heat generating element 34, a time set/monitor 47 for a balloon inflation period (which is also a time set for a valve assembly 50 FIG. 5) to close a proximal extension 16 of a side tube 31 that is used to inflate an inflatable balloon 39, a temperature set knob 48 to set a necessary temperature for treatment, and a display 49 for a setting temperature and an actual temperature that is measured by a temperature sensor 38.

A device 18 is connected to a patient ground plate 20 via a cable 19, to a heat generating element 34 and temperature sensor 38 via cable 15 and to a remote-control box 25 via a cable 21 that is used to supply a remote-control box 25 with power and control signals. A device 18 is preferably hanging on IV Pole 24 of a dialysis machine 23 and receives its power from an auxiliary power socket (not shown for simplicity) of a dialysis machine 23. In another implementation a device 18 receives its power from a wall source and hanging on a standalone IV pole.

Figure 5:
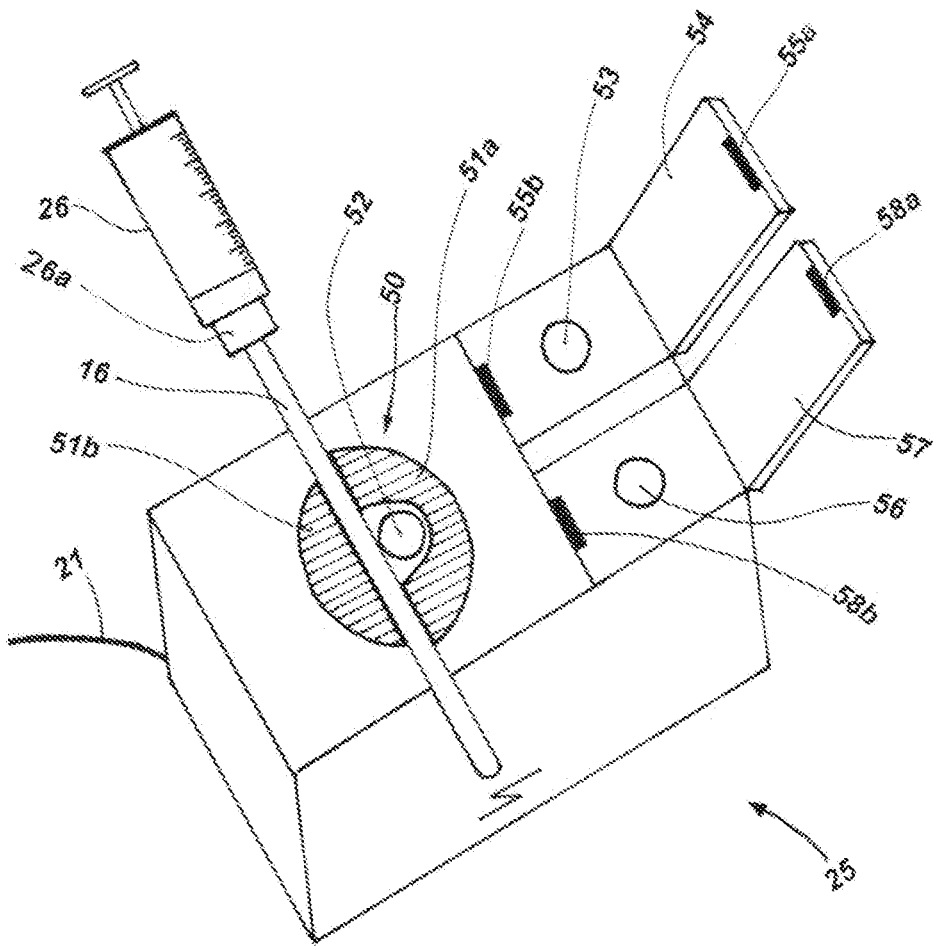
FIG. 5 is an enlarged perspective view of the remote-control box of the system of FIG. 1 according to the present disclosure.

FIG. 5 illustrates an enlarged perspective view of a remote-control box 25 of a system 10 that is located at a nearest point to a patient and is used to activate a radiofrequency energy supplied to a heat generating element 34 for a preset time that has been set on a device 18 using a time set/monitor 46. Pressing a switch 53 to activate a radiofrequency energy supplied to a heat generating element 34.

Also a remote-control box 25 is used to activate a valve mechanism of a valve assembly 50 to rotate a rotation ball 52 to close a proximal extension 16 of a side tube 31, as after the inflation of an inflatable balloon 39 via a proximal extension 16 of a side tube 31 using a syringe 26, and then pressing switch 56 to activate a valve assembly 50 to rotate a rotation ball 52 to close a proximal extension 16 for a preset time to hold an inflatable balloon 39 inflated during that period (this period sets on a devise 18 using a time set/monitor 47).

So, for a patient safety, a heating energy is activated for a certain preset time to avoid deep heat penetration and hence thermal necrosis and also an inflatable balloon 39 is inflated for a certain period of time then disinflated in order to restore a flow of blood through a central vein lumen, this is necessary as a flow of blood may not be stopped for more than 10 to 12 seconds (a period of inflation will be typically last from about 10 to 12 seconds) to avoid any damage to tissues downstream of an inflatable balloon 39. In such cases, it may desirable to repeat a balloon dilation and may be a heating process several times to affect the desired permanent dilation of a stenosis region.

Typically, a temperature may be raised to a final temperature in a range of 80 degrees C. to 140 degrees C., or any suitable temperature. Typically, a heating period may be in a range from 2-45 seconds or any suitable duration.

FIG. 5 also, illustrates a fixation portion 51*a* and 51*b* to fix a proximal extension 16 of a side tube 31, a cover 54 for a switch 53 to avoid pressing a switch 53 accidently, magnets 55*a* and 55*b* to activate a heating mechanism after closing a cover 54 for safety, a cover 57 to cover a switch 56 to avoid pressing switch 56 accidently, magnets 58*a* and 58*b* to active a valve operation after closing a cover 57 for safety, and a cable 21 that is used to connect a remote-control box 25 to a device 18.

FIGS. 6 A-C are illustration showing various steps utilizing in deployment of the catheter 11 of a system 10 in dilating of obstructed blood vessels. In one implementation, a system 10 may be used inside a dialysis unit with a c-arm as a fluoroscopic observation. In another implementation a system 10 may be used in a dialysis unit without a c-arm.

Figure 6A:
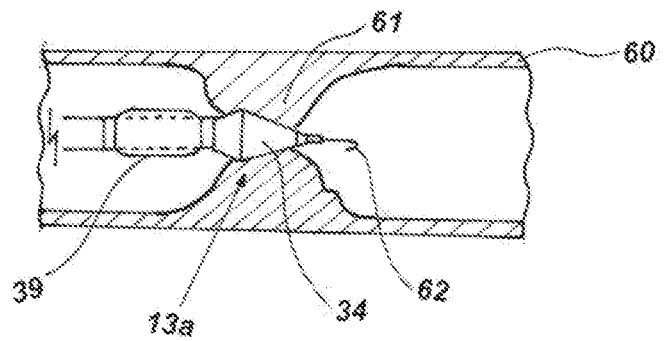
FIGS. 6A-C are illustration showing various steps utilizing in deployment of the catheter of the system of FIG. 1 in performing the method of the present implementation in a blood vessel according to the present disclosure.

The operation and use of a system 10 and a catheter 11 in the method of present implementation for treating occluded vessels in a dialysis unit without c-arm may now be briefly described in connection with an occlusion formed by a stenosis in a blood vessel in connection with illustration shown in FIGS. 6A-6C as follows: 1) a nephrologist connects a system 10 components together as in FIG. 1, then actives a device 18 with an ON/OFF switch 41, then sets a required radiofrequency heating energy on a device 18 using a radiofrequency energy control knob 45 and observes said setting value on a display 43.

Then a nephrologist sets and observes a time period for a heating process of a heat generating element 34 using a time set/monitor 46 on a device 18, then sets and observes a time period to keep an inflatable balloon 39 inflated (it is also a same time to keep a valve 50 closed) using a time set/monitor 47 on a device 18 and then sets a required temperature which it will be a temperature of a heat generating element 34 (which is also a temperature of stenosed tissue around a heat generating element 34) using a temperature set knob 48 and observes a set temperature and an actual temperature monitoring on a screen 49.

A temperature control circuit (not shown for simplicity) inside a device 18 determines how much radiofrequency energy at a maximum should be supplied to a heat generating element 34 to achieve a desired temperature setting without exceeding a radiofrequency heat energy setting on a device 18 by a knob 45. This acts as a double safety for a patient as a first safety is a maximum temperature of a heat generating element 34 that it should not exceed a setting by a temperature knob 48 and a second safety is a maximum radiofrequency energy supplied to a heat generating element 34 that it should not exceed than a radiofrequency energy setting by a radiofrequency energy control knob 45. So, a control circuit (not shown for simplicity) inside a device 18 modulates RF energy applied to a heat generating element 34 according to a signal received from a temperature sensor 38.

Once, an operational parameters are set on a device 18, then a nephrologist 2) locates a remote-control box 25 at a nearest point to a patient for easy operation and locates a patient ground plate 20 in its suitable place, then fixes a proximal extension 16 of a side tube 31 within a valve assembly 50 using fixation portions 51*a* and 51*b*, then connects a syringe with a suitable inflation medium to a coupling assemble 26*a*, then opens covers 54 and 47 of a heat activation switch 53 and a valve control switch 56.

Then, 3) a nephrologist identifies a location of a blood vessel stenosis with respect to a current inserted hemodialysis catheter, let's assume a location of stenosis is located at a tip of an existing catheter which has a length of 30 cm. So, before a removal of an existing catheter, a nephrologist inserts a guide wire 62 into a venous side of an existing catheter, then removes an existing catheter by a conventional technique.

A catheter 11 with a marked length more than 30 cm is then inserted into stenosed blood vessel by employing a sheath and slides it over a guide wire 62 and advances it to a target stenosis which is located at a catheter length of 30 cm as indicated before. So, now a heat generating element 34 of a catheter tip 13*a* is located proximal of stenosis or inside stenosed area 61 of a blood vessel 60 as in FIG. 6A. Then a guidewire 62 is withdrawal. At this stage a syringe 17 which is fixed at a proximal end 14 of a catheter 11 is used to suck some blood to prime an inner tube with a blood to avoid any air embolism.

Then a syringe 17 is filled with a physiologically tolerated flushing liquid, to push such fluid to a tissue downstream of a heat generating element 34. Suitable liquids including a saline solution, a dextrose solution, or an oxygen bearing solution which provide oxygen to a tissue downstream of a heat generation element 34. The introduced liquid can be withdrawal by the syringe 17 after the procedure is over.

Then, 4) a heat activation switch 53 on a remote-control box 25 is then pressed and a cover 54 is closed for magnets 55*a* and 55*b* to activate a heating process for dilating stenosis 61. In one implementation a heating process is followed by a balloon inflation process. In another implementation both processes may be done simultaneously together, in this case an inflatable balloon 39 may be used to occlude a blood vessel during a heating process.

Figure 6B:
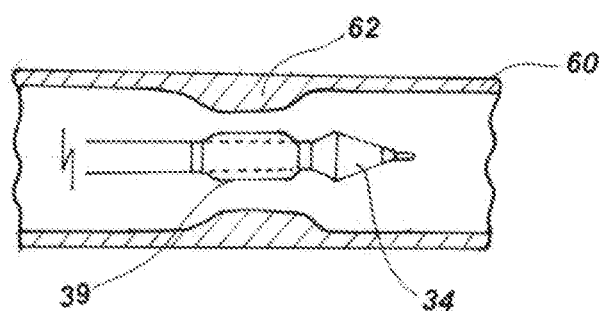

Then, 5) as in FIG. 6B, inflatable balloon 39 is now advanced forward to be located within a heated region of stenosis 62 of a blood vessel 60. A heat generating element 34 is now distal to a heated region of stenosis 62.

Figure 6C:
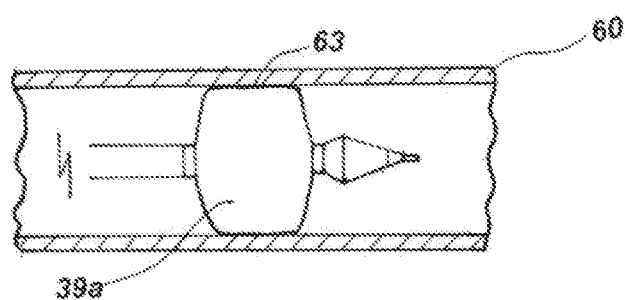

Then 6) as in FIG. 6C inflatable balloon is progressively inflated by introducing a suitable inflation medium such as saline using a syringe 26 to pass through inflatable balloon inflation lumen through a lateral passage 31*a* of a side tube 31. After that a nephrologist presses a switch 56 and close a cover 57 for magnets 58*a* and 58*b* to activate a valve 50 to rotate a rotatable ball 52 to close a proximal extension tube 16 of a side tube 31 to hold an inflatable balloon 39 inflated to a preset time to contact and seal a side wall 63 of a blood vessel 60 to cause compression against a side wall 63 of a blood vessel 60 as in FIG. 6C.

A syringe 17 is used to suck a blood to confirm that a blood flow has been restored to a blood vessel 60 and also to suck any plaque coming off an occlusion forming a stenosis 62. If it is believed that occlusion forming stenosis has been sufficiently compressed and a blood flow has been restored, then a catheter 11 can be removed by a conventional technique after a re-insertion of a guide wire to facilitate the insertion of a new catheter in a same site as now no need to use a new site and re-schedule a patient for a routine dialysis session.

The invention claimed is:

1. A system comprising:
   a catheter comprising a proximal end, a distal end, and elongated portion extending longitudinally therebetween;
      wherein said elongated portion comprises an outer tube, an inner tube, a side tube, two stylets each having a distal end hook, a single radiofrequency lead, and temperature sensor leads extending between said distal and proximal ends of said catheter;
      wherein said distal end of said catheter comprises a distal end of said inner tube, a distal end of said outer tube, a distal end of said side tube, an inflatable balloon, a heat generating element comprising a convectively heated tip and two hooks, a ceramic portion comprising four fixation cavities, a temperature sensor, distal ends of said temperature sensor leads, and a distal end of said single radiofrequency lead connecting to said heat generating element, wherein each of said two stylet distal end hooks and each of said two heat generating element hooks is disposed in a respective cavity of said four cavities to fix said heat generating element to said ceramic portion;
      wherein said proximal end of said catheter comprises a proximal end of said inner tube, a proximal end of said outer tube, a proximal end of said side tube, a proximal extension of said side tube, a proximal end of said two stylets, a proximal end of said single radiofrequency lead, proximal ends of said temperature sensor leads, and a coupling assembly coupled to a syringe;
   a remote-control box comprising a valve assembly, said proximal extension of said side tube, a fixation portion of said proximal extension, a heat activation switch with a cover and magnets, and a valve control switch with a cover and magnets;
   a device comprising a radiofrequency current generator, an OFF/ON switch, an alarm LED, a radiofrequency energy control knob, a display unit for displaying a set radiofrequency energy, a time set/monitor for a heating process, a time set/monitor for balloon inflation, a temperature set knob and a display unit for displaying a set temperature and an actual temperature measured by said temperature sensor,
   wherein said device is connected to a patient ground plate, said heat generating element, said temperature sensor, and said remote-control box.

2. The system of claim 1, wherein said distal end inner tube has a soft tip that is coated by a radiopaque material.

3. The system of claim 1, wherein said heat generating element is axially aligned with said ceramic portion.

4. The system of claim 3, wherein said heat generating element is made of a metal and has a conical shape.

5. The system of claim 3, wherein said heat generating element contacts the temperature sensor and the single radiofrequency lead.

6. The system of claim 3, wherein said heat generating element has an exterior surface that is coated with a non-stick surface.

7. The system of claim 3, wherein said ceramic portion has a smooth surface, a low thermal conductivity, and a distal tip.

8. The system of claim 7, wherein said distal tip of said ceramic portion has a tapered distal end and is coated by a radiopaque material.

9. The system of claim 1, wherein said two stylets are located on each side of said catheter.

10. The system of claim 1, wherein said proximal end of said catheter comprises a coupling assembly that sealingly couples with the syringe.

11. The system of claim 10, wherein said syringe has a tip that fluidly connects a lumen of the syringe to a proximal end of said inner tube via an inner channel of said coupling assembly.

12. The system of claim 1, wherein said proximal extension of said side tube is sealingly coupled with the syringe.

13. A process for treating a site of a stenosed blood vessel in a dialysis patient, comprising:
   the system of claim 1;
   setting operational parameters using said radiofrequency energy control knob, said time set/monitor for the heating process, said time/set monitor for balloon inflation, and said temperature set knob;
   inserting a first guidewire through a venous side of an existing catheter to said site of said stenosed blood vessel;
   marking a length to said site of the existing catheter;
   removing the existing catheter;
   marking the length to said site on the catheter of the system;
   inserting said catheter over said guidewire into said stenosed blood vessel;
   removing said guidewire;
   activating said heating process to convectively heat said heat generating element by pressing said heat activation switch;
   activating a balloon inflation process to dilate said stenosed blood vessel by pressing said valve control switch;
   using the syringe, sucking blood to confirm that blood flow is restored to said stenosed blood vessel;
   re-inserting said guidewire into said catheter after said blood flow is restored;
   removing said catheter;
   inserting a new catheter over said guidewire to said site; and
   rescheduling said patient for a routine dialysis session.

* * * * *